United States Patent
Kanda

(10) Patent No.: US 9,173,630 B2
(45) Date of Patent: Nov. 3, 2015

(54) ULTRASONIC DIAGNOSTIC EQUIPMENT AND CONTROL METHOD THEREFOR

(75) Inventor: Ryoichi Kanda, Otawara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 679 days.

(21) Appl. No.: 11/855,191

(22) Filed: Sep. 14, 2007

(65) Prior Publication Data

US 2008/0221451 A1 Sep. 11, 2008

Related U.S. Application Data

(63) Continuation of application No. PCT/JP2006/305106, filed on Mar. 15, 2006.

(30) Foreign Application Priority Data

Mar. 15, 2005 (JP) ................................ 2005-073788

(51) Int. Cl.
  *A61B 8/00* (2006.01)
  *A61B 8/08* (2006.01)

(52) U.S. Cl.
  CPC *A61B 8/08* (2013.01); *A61B 8/0883* (2013.01)

(58) Field of Classification Search
  USPC ................................................. 600/407, 447
  See application file for complete search history.

(56) References Cited

U.S. PATENT DOCUMENTS

| | | | |
|---|---|---|---|
| 4,913,159 A * | 4/1990 | Gardin et al. | 600/456 |
| 5,010,528 A * | 4/1991 | Ohtsuki et al. | 367/90 |
| 5,429,137 A * | 7/1995 | Phelps et al. | 600/455 |
| 5,441,052 A * | 8/1995 | Miyajima | 600/455 |
| 5,622,174 A | 4/1997 | Yamazaki | |
| 5,669,387 A | 9/1997 | Mine | |
| 5,673,700 A * | 10/1997 | Yamazaki et al. | 600/455 |
| 5,701,897 A * | 12/1997 | Sano | 600/453 |
| 5,709,210 A * | 1/1998 | Green et al. | 600/453 |
| 5,709,211 A * | 1/1998 | Machida | 600/454 |
| 5,769,079 A * | 6/1998 | Hossack | 600/454 |
| 5,785,654 A * | 7/1998 | Iinuma et al. | 600/441 |
| 5,984,881 A * | 11/1999 | Ishibashi et al. | 601/2 |
| 6,017,309 A * | 1/2000 | Washburn et al. | 600/454 |
| 6,030,344 A * | 2/2000 | Guracar et al. | 600/447 |

(Continued)

FOREIGN PATENT DOCUMENTS

| | | |
|---|---|---|
| JP | 6-114059 | 4/1994 |
| JP | 9-201361 | 8/1997 |

(Continued)

OTHER PUBLICATIONS

Journal of Medical Ultrasonics, vol. 30, No. 3, ISSN 1346-1176, (right column, lines 12 to 18, pp. J 383 and J 491.

*Primary Examiner* — Nicholas Evoy

(74) *Attorney, Agent, or Firm* — Oblon, McClelland, Maier & Neustadt, L.L.P.

(57) ABSTRACT

Image data of the interior of a sample (S) are sequentially created on the basis of reception signals at the time when ultrasonic waves are transmitted into the sample (S) so as to scan the interior thereof, movements of respective control points set on the image data are tracked so as to evaluate temporal changes of velocities of motions of the sample (S), and differences of timings of the motions in the sample (S) are color-displayed on the basis of the temporal changes of the velocities.

9 Claims, 7 Drawing Sheets

(56) References Cited

U.S. PATENT DOCUMENTS

| | | | |
|---|---|---|---|
| 6,050,948 A * | 4/2000 | Sasaki et al. | 600/453 |
| 6,086,535 A * | 7/2000 | Ishibashi et al. | 600/439 |
| 6,086,539 A * | 7/2000 | Guracar et al. | 600/453 |
| 6,093,149 A * | 7/2000 | Guracar et al. | 600/447 |
| 6,106,465 A * | 8/2000 | Napolitano et al. | 600/443 |
| 6,110,118 A * | 8/2000 | Guracar et al. | 600/453 |
| 6,176,830 B1 * | 1/2001 | Freiburger | 600/453 |
| 6,177,923 B1 * | 1/2001 | Arenson et al. | 345/589 |
| 6,193,664 B1 * | 2/2001 | Guracar et al. | 600/453 |
| 6,210,168 B1 * | 4/2001 | Aiger et al. | 434/262 |
| 6,241,677 B1 * | 6/2001 | Guracar et al. | 600/453 |
| 6,245,018 B1 * | 6/2001 | Lee | 600/454 |
| 6,258,029 B1 * | 7/2001 | Guracar et al. | 600/453 |
| 6,267,734 B1 * | 7/2001 | Ishibashi et al. | 601/2 |
| 6,277,075 B1 * | 8/2001 | Torp et al. | 600/443 |
| 6,280,402 B1 * | 8/2001 | Ishibashi et al. | 601/2 |
| 6,322,509 B1 * | 11/2001 | Pan et al. | 600/443 |
| 6,322,511 B1 * | 11/2001 | Guracar et al. | 600/453 |
| 6,454,713 B1 * | 9/2002 | Ishibashi et al. | 600/439 |
| 6,464,640 B1 * | 10/2002 | Guracar et al. | 600/453 |
| 6,478,742 B1 * | 11/2002 | Kataoka | 600/449 |
| 6,579,240 B2 * | 6/2003 | Bjaerum et al. | 600/447 |
| RE38,209 E * | 8/2003 | Yamazaki et al. | 600/455 |
| 6,673,020 B2 * | 1/2004 | Okada et al. | 600/454 |
| 6,679,847 B1 * | 1/2004 | Robinson et al. | 600/447 |
| 6,682,483 B1 * | 1/2004 | Abend et al. | 600/437 |
| 6,719,697 B2 * | 4/2004 | Li | 600/454 |
| 6,733,454 B1 * | 5/2004 | Bakircioglu et al. | 600/453 |
| 6,860,854 B2 * | 3/2005 | Robinson | 600/447 |
| 7,044,913 B2 * | 5/2006 | Shiki | 600/454 |
| 7,343,031 B2 * | 3/2008 | Pedrizzetti et al. | 382/128 |
| 2003/0013962 A1 * | 1/2003 | Bjaerum et al. | 600/443 |
| 2003/0045795 A1 * | 3/2003 | Bjaerum et al. | 600/441 |
| 2003/0083578 A1 * | 5/2003 | Abe et al. | 600/447 |
| 2003/0125624 A1 * | 7/2003 | Shiki | 600/443 |
| 2004/0019278 A1 * | 1/2004 | Abend | 600/454 |
| 2004/0116810 A1 * | 6/2004 | Olstad | 600/443 |
| 2004/0143189 A1 * | 7/2004 | Lysyansky et al. | 600/450 |
| 2004/0249281 A1 * | 12/2004 | Olstad | 600/437 |
| 2005/0033175 A1 * | 2/2005 | Lee et al. | 600/453 |
| 2007/0167771 A1 * | 7/2007 | Olstad | 600/437 |

FOREIGN PATENT DOCUMENTS

| | | |
|---|---|---|
| JP | 10-262970 | 10/1998 |
| JP | 3187008 | 5/2001 |
| JP | 2004-529719 | 9/2004 |
| WO | WO 02/095683 A2 | 11/2002 |

* cited by examiner

ULTRASONIC DIAGNOSTIC EQUIPMENT AND CONTROL METHOD THEREFOR

CROSS REFERENCE TO RELATED APPLICATIONS

This is a Continuation Application of PCT Application No. PCT/JP2006/305106, filed Mar. 15, 2006, which was published under PCT Article 21(2) in Japanese.

This application is based upon and claims the benefit of priority from prior Japanese Patent Application No. 2005-073788, filed Mar. 15, 2005, the entire contents of which are incorporated herein by reference.

BACKGROUND OF THE INVENTION

1. Field of the Invention

The present invention relates to an ultrasonic diagnostic equipment which transmits ultrasonic pulses into a sample so as to scan the interior of the sample, and which receives reflected waves from the sample, thereby to acquire the motion information of a tissue on the basis of the image of the interior of the sample, and a control method for the ultrasonic diagnostic equipment.

2. Description of the Related Art

An ultrasonic diagnostic equipment noninvasively obtains the tomographic image of a soft tissue in a living body, from the surface of the body by an ultrasonic pulse echo method. The ultrasonic diagnostic equipment transmits ultrasonic waves from an ultrasonic probe into a sample, it receives reflected waves created by the mismatching of acoustic impedances within the sample, by the ultrasonic probe so as to generate a reception signal, and it images the interior of the sample on the basis of the reception signal.

As compared with other medical image equipment, the ultrasonic diagnostic equipment has the following merits: By way of example, the ultrasonic diagnostic equipment is small-sized and inexpensive. It affords a high safety without exposure to X-rays etc. It is capable of blood flow imaging. This ultrasonic diagnostic equipment is employed for the diagnoses of, for example, the heart and the abdomen, and it is extensively utilized in urology, obstetrics and gynecology, etc. It has been known that the ultrasonic diagnostic equipment is useful for the diagnosis of the heart. It is very useful to objectively and quantitatively estimate the function of the tissue of the living body, such as a cardiac muscle.

As a remedy which is recently spotlighted, there is mentioned a cardiac resynchronization therapy (CRT) for the patients of serious cardiac failure. It has been attempted to employ the ultrasonic diagnostic equipment for the quantitative estimation for deciding the applicability of the cardiac resynchronization therapy or for deciding the effect of the medical treatment.

The cardiac resynchronization therapy will be briefly explained. The patient of serious cardiac failure often accompanies the contraction dyssynchrony of a cardiac wall motion. The heart is being moved by the conduction of electric signals. An intraventricular conduction disturbance sometimes arises in the patient of the serious cardiac malady. The intraventricular conduction disturbance is the occurrence of a deviation in a sequence in which the electric signals moving the cardiac muscle are conveyed. In a ventricle in which the electric signals ought to be conveyed substantially simultaneously over the entirety, the intraventricular conduction disturbance sometimes develops a part to which the electric signal is conveyed earlier and a part to which the electric signal is conveyed later, on account of the deviation. As a result, the contraction of the cardiac wall is not synchronized, and the heart fails to pump out blood sufficiently, to fall into the state of the cardiac failure.

The cardiac resynchronization therapy is the medical treatment in which an electric signal is artificially issued to such a disturbance, whereby the sequence of the electric signals to be conveyed to the heart is adjusted to assist in the pump function of the heart. Concretely, the medical treatment is done by embedding a pacemaker under the skin of the breast. The cardiac resynchronization therapy has already been performed for a large number of patients, and dramatic improvements in the symptoms have been verified.

On the other hand, there are cases as to which the improvements in the symptoms are not observed even when the cardiac resynchronization therapy is applied. The cases are cardiac failure ones. The patients of such cardiac failure cases have been verified to amount to about 30% of all patients. This is because whether or not the cause of the cardiac failure cases is the contraction dyssynchrony cannot be exactly judged.

In the present situation, the application criteria of the cardiac resynchronization therapy are stipulated to be less than 130 msec in the QRS width of an electrocardiogram waveform and to be 35% in the left ventricular ejection fraction (EF). In accordance with the criteria, patients who suffer from the cardiac failure, but who do not suffer from the contraction dyssynchrony are also included.

Therefore, there has been developed a technique which is intended to extract only the contraction dyssynchrony by a quantitative estimation method employing the ultrasonic diagnostic equipment. The technique is disclosed in, for example, the official gazette of JP-A-10-262970. The official gazette of JP-A-10-262970 discloses to detect the motion velocity of a cardiac muscle (cardiac wall) by a Doppler method, and to calculate and analyze this motion velocity. The technique can automatically detect the peaks of the changes-with-time of motion velocities, displacements or the likes at the pluralities of parts of the cardiac muscle. In addition, the technique calculates time periods from a predetermined cardiac phase till arrivals at the individual peaks and then colors the ultrasonic image of the cardiac muscle in accordance with the time periods. Thus, the differences of the motion states of the whole cardiac muscle are outputted as color images. The differences of motion timings at the respective parts of the cardiac muscle can be imaged.

The ultrasonic diagnostic equipment has realized to image, not only a structure within a living body, but also the movement velocity of a tissue, by a tissue Doppler method. The tissue Doppler method measures the velocity of a part of intense reflection and comparatively slow movement, such as cardiac wall, and it presents a two-dimensional color display. In recent years, techniques for obtaining clinically more important information have been proposed by applying the function of imaging the movement velocity of the tissue by the tissue Doppler method. The techniques are, for example, the imaging of movement timings as employs the movement velocity distribution image of the tissue, velocity gradient imaging, displacement imaging, strain imaging, and tissue tracking which employs angular corrections.

The imaging of the movement timings as employs the movement velocity distribution image of the tissue performs the color coding of time periods in which the tissue movement velocities of individual pixels arrive at a certain threshold value or at peaks, by employing the movement velocity distribution image of the tissue as obtained by the tissue Doppler method. Thus, the movement timings of the tissue are imaged. This imaging is disclosed in, for example, the official gazette of Japanese Patent No. 3,187,008.

The velocity gradient imaging acquires a local velocity gradient in such a way that the velocity difference of two points spaced a predetermined distance, as to a movement velocity distribution obtained by the tissue Doppler method, is divided by the distance between the two points. In addition, this imaging acquires such local velocity gradients at the large number of points of the image so as to display the acquired gradients as an image.

The displacement imaging computes the quantity of the movements of the tissue by integrating values obtained in such a way that the velocity values of individual frames included in a predetermined time period are multiplied by an interframe time difference, as to a movement velocity distribution obtained by the tissue Doppler method.

The strain imaging obtains the strain distribution image of the tissue by employing the movement quantity distribution image obtained by the displacement imaging, or the velocity gradient image.

In obtaining the displacement image or the strain image, an integration process employing the values of a plurality of frames is required. As is usually considered, the integration of the values of the same pixels of the plurality of frames does not become the integration of the value of the same tissue as to the moving tissue. The tissue tracking which employs the angular corrections need to integrate the values while tracking the movements of the tissue.

BRIEF SUMMARY OF THE INVENTION

However, problems to be stated below are involved in the imaging of the movement timings.

In the first place, the tissue is moving. For this reason, when the velocity values of the same pixels in the individual frames are employed, the time of the maximum velocity of the same tissue is not displayed. By way of example, the short-axis image of the heart will be considered. FIG. 11 shows a model diagram of, for example, the left ventricular short-axis image of the heart as is a sample S displayed on, for example, a monitor. $US_1$ denotes the outer membrane of the left ventricular short-axis image of the heart. $US_2$ denotes the inner membrane of the left ventricular short-axis image at the endodiastole of the heart. $US_3$ denotes the inner membrane of the left ventricular short-axis image at the endosystole of the heart.

A point "A" is set in the short-axis image of the heart. In a case where the cardiac muscle of the left ventricle has moved in the short-axis image, the point A lies in a cardiac cavity at the endodiastole. This point A lies in the cardiac muscle at the endosystole. FIG. 12 shows the velocity change of a systolic motion at the time when the cardiac muscle of the left ventricle has moved in the short-axis image. The temporal change of the velocity of the point A reflects the velocity of the cardiac muscle in the latter half. In contrast, the temporal change of the velocity of the point A becomes the velocity within the cardiac cavity, in the first half. Therefore, the peak of the movement velocity of the cardiac muscle is not correctly detected.

Secondly, the peaks of the changes-with-time of motion velocities, displacements or the likes at a plurality of parts of the cardiac muscle are automatically detected. FIG. 13 shows the change of the velocity of a certain part of the cardiac muscle versus the lapse of time. The change of the velocity exhibits flatness near a top. In such a case where the change of the velocity is flat near the top, the time of a peak position sometimes moves greatly due to a slight fluctuation.

Thirdly, the way how the movement velocity changes might be clinically useful. Whether the cardiac muscle has contracted abruptly in a short time or has contracted slowly in a comparatively long time, is not known from a peak time.

Fourthly, the velocity is influenced by ambient cardiac muscles. The velocity reflects the movement of the cardiac muscle. The velocity does not reflect if the particular part of the cardiac muscle has contracted. In case of, for example, an apical image, the movement velocity of any limited part of the cardiac muscle is determined by the contraction of the whole part which extends from an apex to the limited part. The movement velocity of the limited part of the cardiac muscle does not represent the strength of the contraction of the particular part. Accordingly, as an index which represents the contraction timing of the limited part, it is not always appropriate to employ the velocity.

Fifthly, the peak of the velocity represents a time at which the contraction is the most active, and it does not represent the completion time of the contraction. By way of example, the time at which the cardiac muscle is contracting most actively is known. However, the time when the systolic phase has ended is not known.

Heretofore, any of the velocity gradient imaging, the displacement imaging, the strain imaging, and the tissue tracking which employs the angular corrections has been sometimes used. Also in these cases, a technique whose precision is high and which can image a timing concerning the movement or transformation of a tissue has been eagerly desired.

An object of the present invention is to provide an ultrasonic diagnostic equipment whose precision is high and which can image a timing concerning the movement or transformation of a tissue, and a control method for the equipment.

An ultrasonic diagnostic equipment according to the first aspect of the invention comprises a scan unit which transmits ultrasonic waves into a sample, which receives reflected waves from the sample, and which outputs reception signals; and an arithmetic/display unit which evaluates temporal changes of velocities of motions of the sample on the basis of the reception signals outputted from the scan unit, and which displays differences of timings of the motions in the sample on the basis of the temporal changes of the velocities.

An ultrasonic diagnostic equipment according to the second aspect of the invention comprises a scan unit which transmits ultrasonic waves into a sample, which receives reflected waves from the sample, and which outputs reception signals; a detection unit which detects velocities of motions of the sample on the basis of the reception signals outputted from the scan unit; and an arithmetic/display unit which evaluates at least one sort of strain values, velocity gradient values and displacement values on the basis of the velocities of the motions of the sample as have been detected by the detection unit, and which displays differences of timings of the motions in the sample on the basis of changes of the evaluated values.

A control method for an ultrasonic diagnostic equipment according to another aspect of the invention transmits ultrasonic waves from a scan unit into a sample, receives reflected waves from the sample and outputs reception signals, evaluates temporal changes of velocities of motions of the sample on the basis of the reception signals outputted from the scan unit, and displays differences of timings of the motions in the sample on the basis of the temporal changes of the velocities.

DETAILED DESCRIPTION OF THE INVENTION

Now, the first embodiment of the present invention will be described with reference to the drawings.

Figure 1:
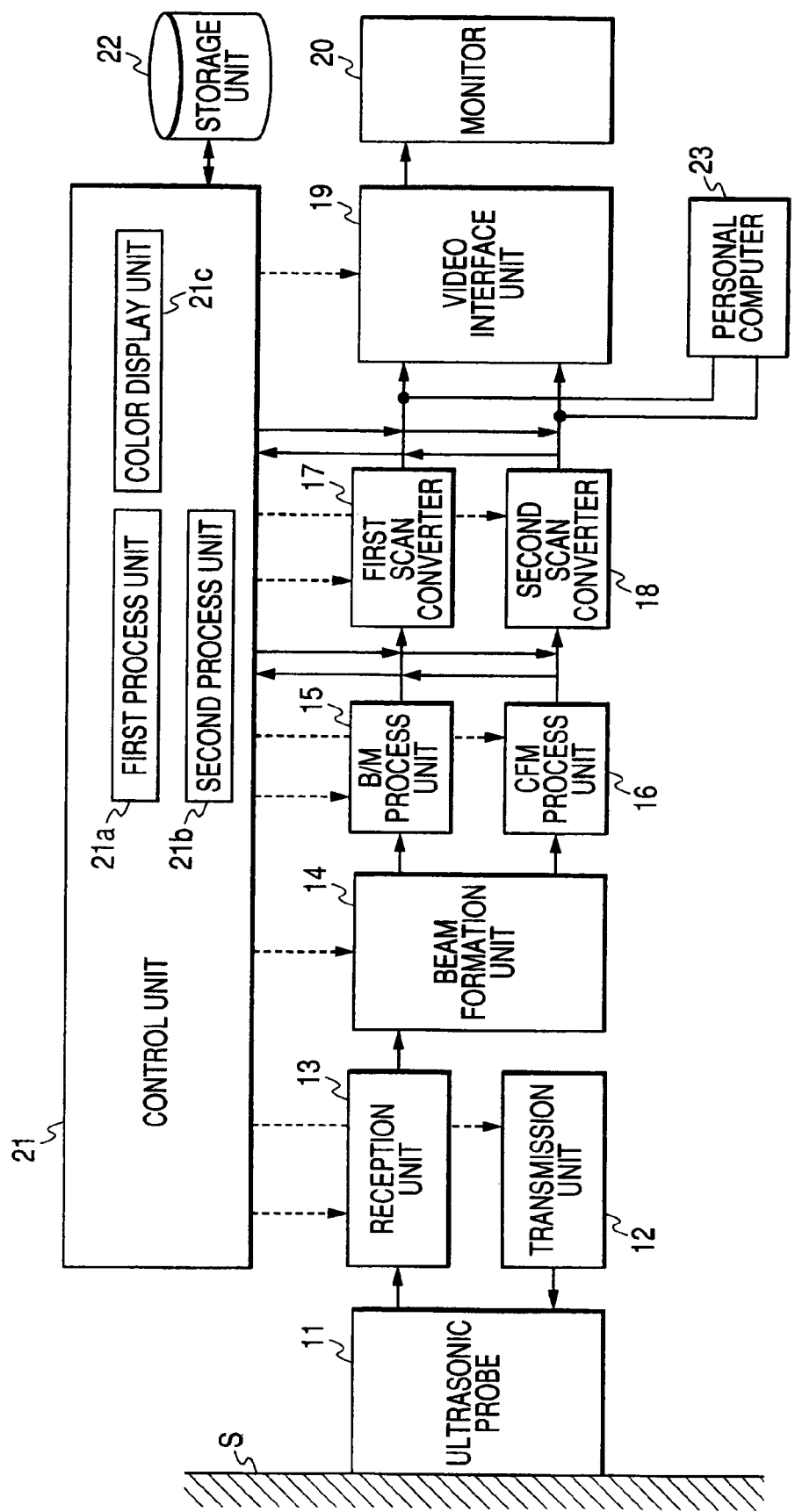
FIG. 1 is a block arrangement diagram showing the first embodiment of an ultrasonic diagnostic equipment according to the present invention.

FIG. 1 shows a block arrangement diagram of an ultrasonic diagnostic equipment. A transmission unit 12 and a reception unit 13 are connected to an ultrasonic probe 11. The ultrasonic probe 11 includes a plurality of piezoelectric transducers, matching layers which are disposed for the respective piezoelectric transducers, backing members which prevent ultrasonic waves from being propagated backward from the respective piezoelectric transducers, and so forth. The respective piezoelectric transducers generate ultrasonic pulses on the basis of drive signals from the transmission unit 12, and they receive reflected waves from a sample S and convert the waves into electric signals. Accordingly, the ultrasonic probe 11 transmits the ultrasonic pulses into, for example, the sample S. The ultrasonic pulses transmitted into the sample S are successively reflected at the discontinuous surfaces of acoustic impedances in the sample S, such as "in vivo" tissues and blood flows, and the resulting reflected waves enter the ultrasonic probe 11. The ultrasonic probe 11 receives the reflected waves, and converts the received waves into the electric signals so as to output the signals.

The transmission unit 12 delivers the drive signals to the respective piezoelectric transducers of the ultrasonic probe 11, so as to generate the ultrasonic pulses. The transmission unit 12 controls the phases of the drive signals to be delivered to the respective piezoelectric transducers, within a preset fixed range. The transmission unit 12 phase-controls the drives of the respective piezoelectric transducers, and causes the transmitted ultrasonic pulses to scan the sample.

The reception unit 13 amplifies and outputs the electric signals from the ultrasonic probe 11.

A beam formation unit 14 digitally converts the electric signals outputted from the reception unit 13 and delays the digital electric signals predetermined time periods, and it thereafter subjects the electric signals to a phasing addition and focusing. The beam formation unit 14 feeds the focused signal to a B/M (B-mode/M-mode) process unit 15 and a CFM (color Doppler mode) process unit 16.

The B/M process unit 15 subjects the output signal of the beam formation unit 14 to band-pass filtering, and it thereafter detects the envelope component of the resulting signal and executes a LOG compression process for the component. The B/M process unit 15 may well execute a process such as edge emphasis.

The CFM process unit 16 subjects the output signal of the beam formation unit 14 to high-pass filtering, and it thereafter executes an autocorrelation process. The high-pass filtering separates tissue signals and blood flow signals. The high-pass filtering is executed by, for example, using an MTI filter or a Wall filter. The invention is premised on a tissue Doppler method. In this case, the MTI filter becomes an all-frequency-pass or low-pass filter. Thus, the MTI filter passes the tissue signals. Otherwise, the high-pass filtering sometimes executes a nonlinear process for reducing or removing the tissue signals. The autocorrelation process detects the movement velocity of the blood flow or the tissue.

A first scan converter 17 maps the output signals of the B/M process unit 15 to positions corresponding to the transmissions/receptions of the ultrasonic pulses, and sequentially creates a plurality of image data every frame.

A second scan converter 18 maps the output signals of the CFM process unit 16 to the positions corresponding to the transmissions/receptions of the ultrasonic pulses, and sequentially creates a plurality of image data every frame.

A video interface unit 19 receives the image data for the B/M as are outputted from the first scan converter 17, or the image data for the CFM as are outputted from the second scan converter 18, and it combines these image data with various information items on an image, so as to display the laid-out ultrasonic image on a monitor 20.

A control unit 21 controls the transmission unit 12, reception unit 13, beam formation unit 14, B/M process unit 15, CFM process unit 16, first scan converter 17, second scan converter 18 and video interface unit 19. The control unit 21 accepts the output signal of the B/M process unit 15, the output signal of the CFM process unit 16, and the image data which are respectively outputted from the first and second scan converters 17 and 18.

The control unit 21 sets as control points, pixels on the image data sequentially created by the first scan converter 17 and the second scan converter 18, it tracks the movements of the control points on the image data of respective frames created in succession, and it executes the correlation process between the image data of the respective frames, thereby to evaluate the velocities of the control points, and it displays the differences of the timings of motions in the sample S, on the monitor 20 on the basis of the changes of the velocities.

The control unit 21 sets the control points at all pixels or some pixels in the image data.

The control unit 21 includes a first process unit 21a, a second process unit 21b and a color display unit 21c which are arithmetic/display units. The first process unit 21a evaluates the peak positions of the changes of the velocities of the motions of the tissue of the sample S versus the lapse of time.

The second process unit 21b evaluates the differences of the timings of the motions of the tissue as based on the systolic motion of the sample S, on the basis of the individual peak positions obtained by the first process unit 21a.

The second process unit 21b displays the ultrasonic image on the monitor 20 on the basis of the image data which are sequentially created by the first scan converter 17 and the second scan converter 18. The second process unit 21b displays the differences of the timings of the motions of the tissue as based on the systolic motion of the sample S, in juxtaposed fashion by way of example, on the ultrasonic image displayed on the monitor 20. Thus, the second process unit 21b displays whether the motions of the tissues of the sample S are abrupt or slow.

The color display unit 21c color-displays on the monitor 20, the differences of the timings of the motions of the tissue of the sample S as have been obtained by the second process unit 21b.

The control unit 21 may well receive the respective output signals of the B/M process unit 15 and CFM process unit 16 and perform a scan conversion so as to analyze the differences of the timings of the motions of the tissue of the sample S.

Incidentally, a storage unit 22 is connected to the control unit 21. The image data which are sequentially created by the first scan converter 17 and the second scan converter 18, are sent to a personal computer 23.

Next, the operation of the equipment configured as described above will be described.

First, when a diagnostic process for the sample S is started, the transmission unit 12 delivers drive signals to the individual piezoelectric transducers of the ultrasonic probe 11. On this occasion, the transmission unit 12 controls the phases of the drive signals to be delivered to the respective piezoelectric transducers, within a preset fixed range. Thus, the ultrasonic probe 11 transmits ultrasonic pulses into, for example, the sample S so as to scan this sample. The ultrasonic pulses transmitted into the sample S are successively reflected at the discontinuous surfaces of acoustic impedances in the sample S, such as "in vivo" tissues and blood flows, and the resulting reflected waves enter the ultrasonic probe 11. The ultrasonic probe 11 receives the reflected waves, and converts the received waves into electric signals so as to output the signals. The reception unit 13 amplifies and outputs the electric signals from the ultrasonic probe 11.

The beam formation unit 14 digitally converts the electric signals outputted from the reception unit 13 and delays the digital electric signals predetermined time periods, and it thereafter subjects the electric signals to a phasing addition and focusing.

The B/M process unit 15 subjects the output signal of the beam formation unit 14 to band-pass filtering, and it thereafter detects the envelope component of the resulting signal and executes a LOG compression process for the component.

Simultaneously therewith, the CFM process unit 16 subjects the output signal of the beam formation unit 14 to high-pass filtering by, for example, an MTI filter, thereby to separate the output signal into tissue signals and blood flow signals. Subsequently, the CFM process unit 16 executes an autocorrelation process for the tissue signals and the blood flow signals, thereby to detect the movement velocity of the blood flows or the tissues.

The first scan converter 17 maps the output signals of the B/M process unit 15 to positions corresponding to the transmissions/receptions of the ultrasonic pulses, and sequentially creates a plurality of image data every frame.

Simultaneously therewith, the second scan converter 18 maps the output signals of the CFM process unit 16 to the positions corresponding to the transmissions/receptions of the ultrasonic pulses, and sequentially creates a plurality of image data every frame.

The video interface unit 19 receives the image data for the B/M as are outputted from the first scan converter 17, or the image data for the CFM as are outputted from the second scan converter 18, and it combines these image data with various information items on an image, so as to display the laid-out ultrasonic image of the interior of the sample S on the monitor 20.

Figure 11:
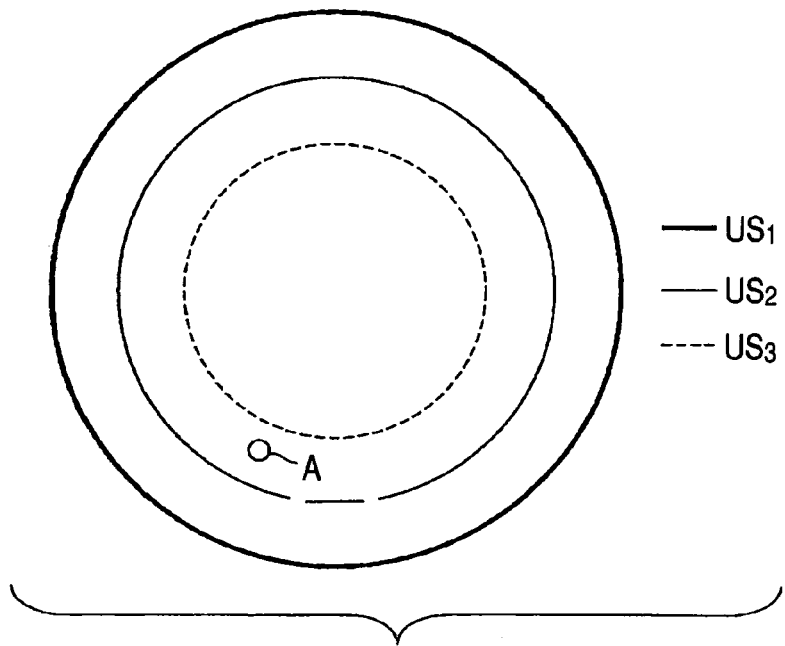
FIG. 11 is a model diagram of a monitor display example of that left ventricular short-axis image of the heart which has been created by the equipment.
Figure 12:
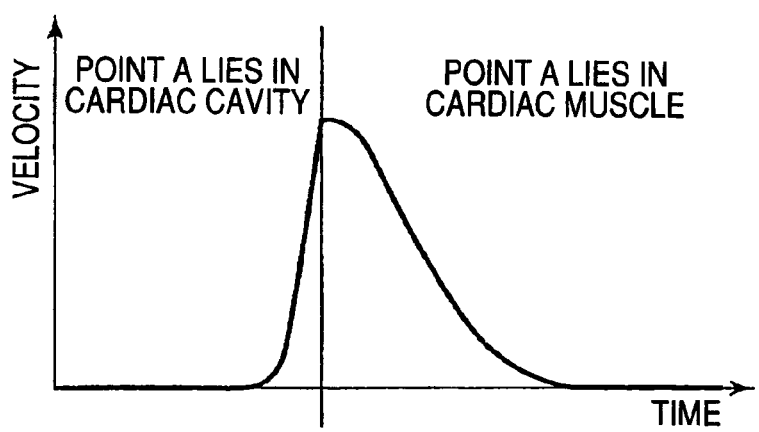
FIG. 12 is a diagram showing the velocity change of a systolic motion at the time when the cardiac muscle of the left ventricle has moved in the short-axis image.
Figure 13:
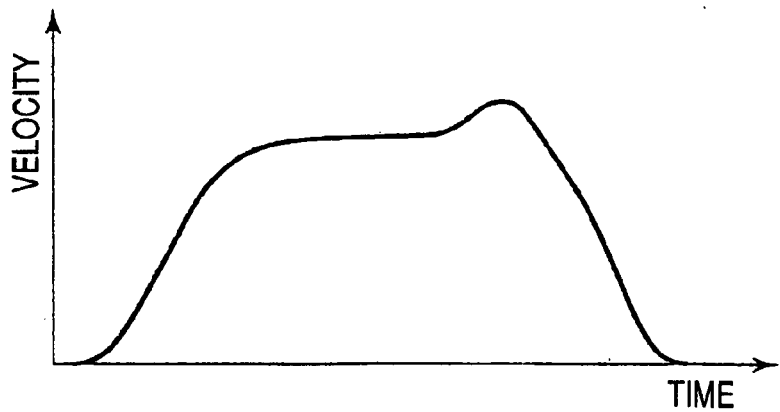
FIG. 13 is a diagram showing the change of the velocity of a certain part of the cardiac muscle versus the lapse of time.

FIG. 11 shows a model diagram of the left ventricular short-axis image of, for example, the heart being the sample S displayed on the monitor 20. $US_1$ denotes the outer membrane of the left ventricular short-axis image of the heart. $US_2$ denotes the inner membrane of the left ventricular short-axis image at the endodiastole of the heart. $US_3$ denotes the inner membrane of the left ventricular short-axis image at the endosystole of the heart. A point "A" is set in the short-axis image of the heart. In a case where the cardiac muscle of the left ventricle has moved in the short-axis image, the point A lies in a cardiac cavity at the endodiastole. This point A lies in the cardiac muscle at the endosystole. FIG. 12 shows the velocity change of a systolic motion at the time when the cardiac muscle of the left ventricle has moved in the short-axis image. The temporal change of the velocity of the point A reflects the velocity of the cardiac muscle in the latter half. In contrast, the temporal change of the velocity of the point A becomes the velocity within the cardiac cavity, in the first half. Therefore, the peak of the movement velocity of the cardiac muscle is not correctly detected.

Figure 2:
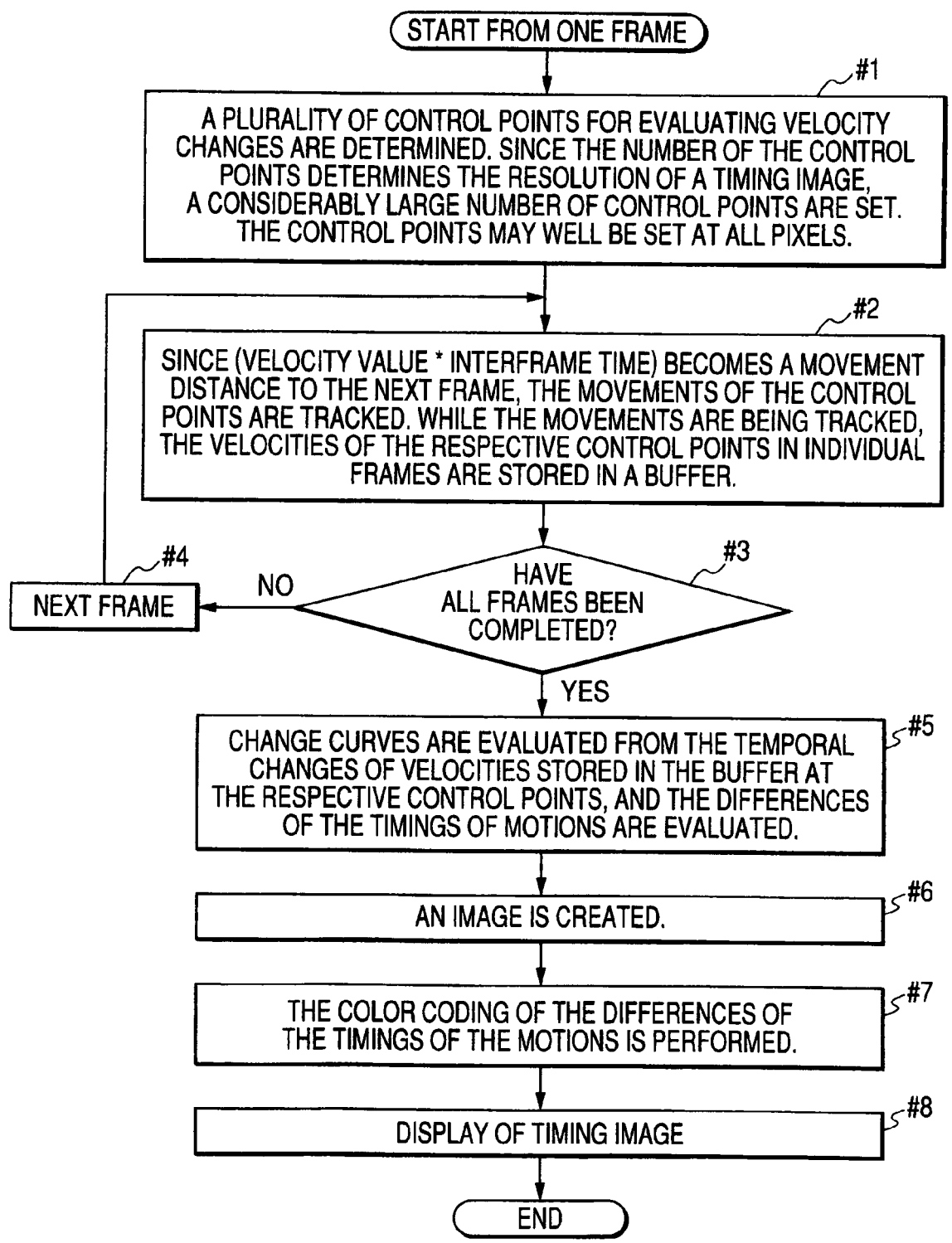
FIG. 2 is a control-process flow chart in the equipment.

To cope with this, the control unit 21 of this embodiment executes a control-process flow chart shown in FIG. 2.

The control unit 21 accepts the image data of individual frames as are created by the first and second scan converters 17 and 18, and it temporally stores the image data in, for example, the storage unit 22. At a step #1, the control unit 21 automatically sets control points at all the pixels of the image data of one frame accepted from each of the first and second scan converters 17 and 18. Incidentally, the control unit 21 may well set control points at pixels which constitute at least some of the image data of one frame. In the ensuing description, however, only two control points shall be referred to for the sake of convenience.

Figure 3:
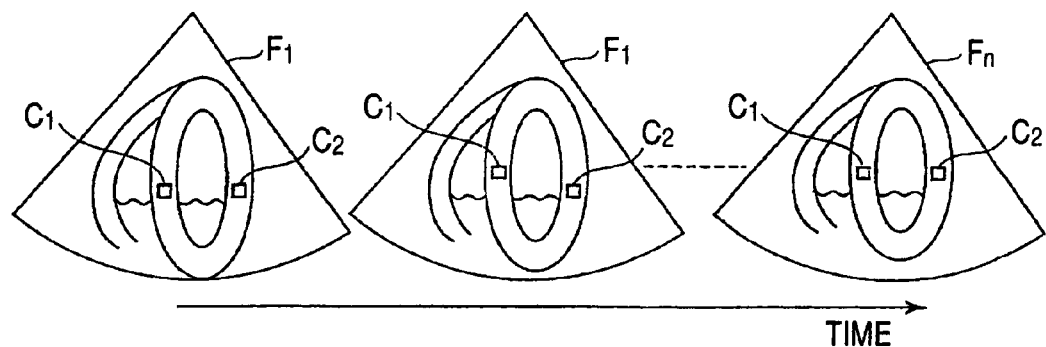
FIG. 3 is a diagram showing two control points which have been set on image data in the equipment.

FIG. 3 shows the two control points $C_1$ and $C_2$ set on the image data of a frame $F_1$. These control points $C_1$ and $C_2$ are set in order to evaluate the change of a velocity at which a tissue moves on the basis of the systolic motion of the heart.

Subsequently, at a step #2, the control unit 21 tracks the movements of the respective control points $C_1$ and $C_2$ on the image data of a frame $F_2$ which is created later than the frame $F_1$. The control points $C_1$ and $C_2$ track the same tissue of the heart on the image data of the respective frames $F_1$ and $F_2$. The tracking is performed using velocity information obtained by the tissue Doppler method. Thus, the movements of the respective control points $C_1$ and $C_2$ between the image data of the frames $F_1$ and $F_2$ are tracked.

The control unit 21 evaluates the velocity values of the respective control points $C_1$ and $C_2$ on the basis of the movement distances of these control points $C_1$ and $C_2$ on the image data of the frames $F_1$ and $F_2$ and the interval of the image data of the frames $F_1$ and $F_2$. Incidentally, the movement distance between the frames is evaluated by the following formula:

$$\text{Movement distance to Next frame} = \text{Velocity value} \times \text{Interframe time (Constant)} \quad (1)$$

The control unit 21 stores the velocity values of the respective control points $C_1$ and $C_2$ in, for example, the storage unit 22.

Subsequently, at a step #3, the control unit 21 judges whether or not the evaluations of the velocity values of the respective control points $C_1$ and $C_2$ on the image data of all frames $F_1$-$F_n$ have been completed. If, as the result of the judgment, the evaluations have not been completed, the control unit 21 returns from a step #4 to the step #2, and it tracks the respective control points $C_1$ and $C_2$ on the image data of the frame $F_2$ and the next frame $F_3$. Thus, the control unit 21 evaluates the velocity values of the respective control points $C_1$ and $C_2$ on the basis of the movement distances of the respective control points $C_1$ and $C_2$ on the image data of the frames $F_2$ and $F_3$ and the interval of the image data of the frames $F_1$-$F_n$. The control unit 21 stores the velocity values of the respective control points $C_1$ and $C_2$ in, for example, the storage unit 22.

Thenceforth, the control unit 21 similarly iterates the steps #2 through #4, and it tracks the respective control points $C_1$ and $C_2$ between the image data of all the frames $F_1$-$F_n$, so as to evaluate the velocity values of these control points $C_1$ and $C_2$. The control unit 21 stores the individual velocity values of the respective control points $C_1$ and $C_2$ in, for example, the storage unit 22. Incidentally, the individual velocity values of the respective control points in all the pixels in the image data of all the frames $F_1$-$F_n$ are stored in the storage unit 22.

When the velocity values of the respective control points $C_1$ and $C_2$ between the image data of all the frames $F_1$-$F_n$ have been evaluated, the control unit 21 operates at a step #5 to read out the velocity values of the respective control points $C_1$ and $C_2$ between the image data of all the frames $F_1$-$F_n$ as have been stored in the storage unit 22, and to evaluate the temporal changes of the velocities of the respective control points $C_1$ and $C_2$.

Figure 4:
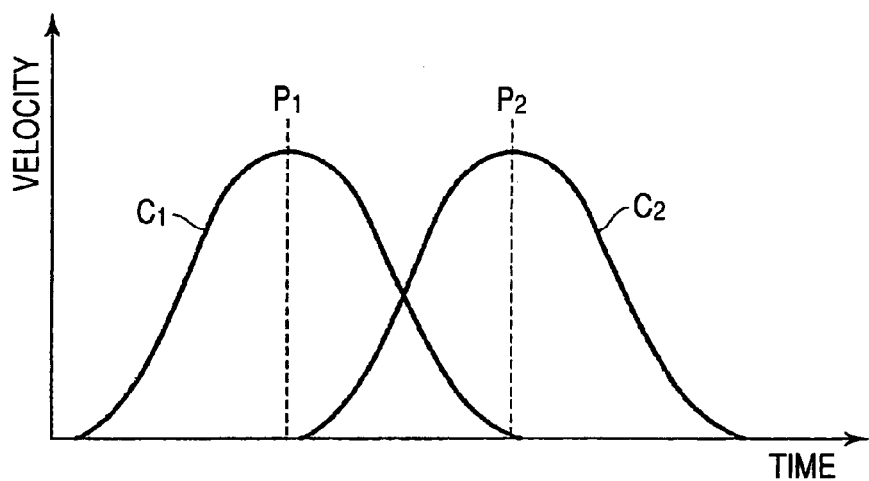
FIG. 4 is a diagram showing peak positions in the change curves of the respective control points versus the lapse of time, in the heart of the contraction dyssynchrony of a cardiac wall motion, the change curves being obtained by the equipment.

FIG. 4 shows the change curves of the velocities of the respective control points $C_1$ and $C_2$ versus the lapse of time. The change curves indicate the changes of the velocities of the motions of the heart at the respective control points $C_1$ and $C_2$. It is seen from the figure that, in the systolic motion of the heart, the tissue observed at the control point $C_2$ moves later than the tissue observed at the control point $C_1$.

The change curves of the control points have been obtained at all the pixels in the image data of all the frames $F_1$-$F_n$. Thus, the change curves of the respective control points in the whole heart being the sample S are obtained.

The first process unit 21a evaluates the peak positions in the individual change curves of the two control points $C_1$ and $C_2$. FIG. 4 shows the peak positions $P_1$ and $P_2$ in the change curves of the respective control points $C_1$ and $C_2$. In the figure, the peak positions $P_1$ and $P_2$ are different.

The second process unit 21b evaluates the difference of the timings of the tissue motions based on the systolic motion of the sample S, on the basis of the peak positions evaluated by the first process unit 21a. The second process unit 21b may well display on the monitor 20, the peak positions $P_1$ and $P_2$ in the change curves of the respective control points $C_1$ and $C_2$ as shown in FIG. 4. It is seen that, since the peak positions $P_1$ and $P_2$ are different, the timings of the tissue motions in the systolic motion of the sample S, at the respective control points $C_1$ and $C_2$ are different. It can be diagnosed as the contraction dyssynchrony of the cardiac wall motion that the timings of the tissue motions based on the systolic motion of the heart are different.

Figure 5:
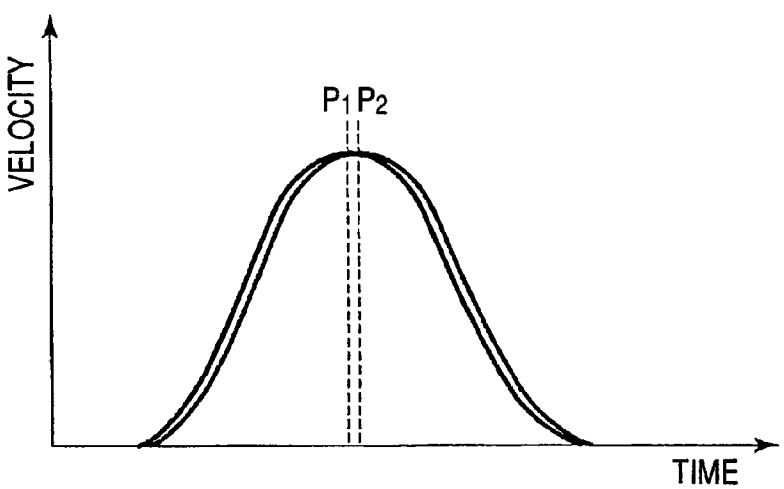
FIG. 5 is a diagram showing peak positions in the change curves of respective control points versus the lapse of time, in the normal heart as is obtained by the equipment.

Incidentally, FIG. 5 shows peak positions $P_1$ and $P_2$ in the change curves of two control points $C_1$ and $C_2$ in the normal heart. In the figure, the peak positions $P_1$ and $P_2$ are substantially the same. Thus, it is seen that the timings of tissue motions based on the systolic motion of the sample S, at the respective control points $C_1$ and $C_2$ are substantially the same.

Subsequently, at a step #6, the control unit 21 creates the image data of the movements of, for example, the respective control points $C_1$ and $C_2$, on the basis of all the change curves including the respective control points $C_1$ and $C_2$ as have been evaluated at all the pixels of the image data.

Subsequently, at a step #7, the color display unit 21c performs the color coding of the differences of the timings of the tissue motions based on the systolic motion of the heart being the sample S, on the basis of all the change curves including the respective control points $C_1$ and $C_2$ as have been evaluated at all the pixels of the image data, so as to display a timing image on the monitor 20.

Figure 6:
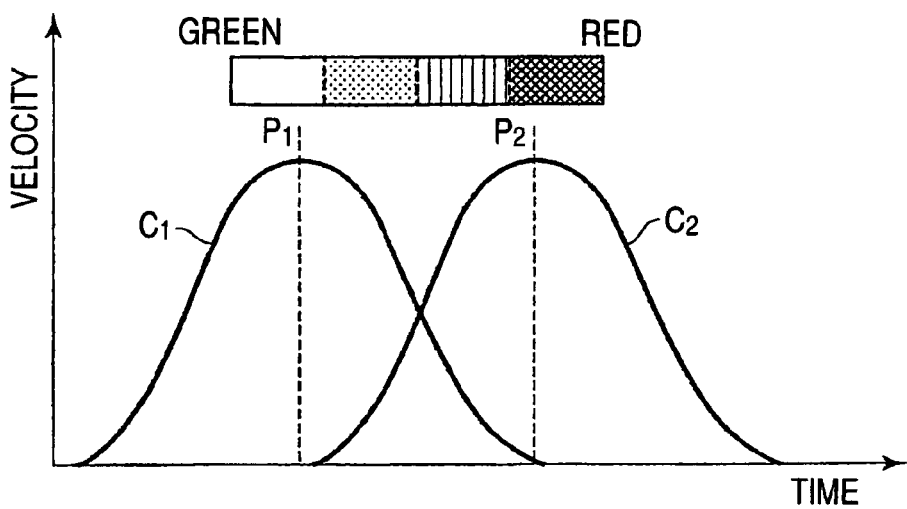
FIG. 6 is a diagram showing color coding which employs a color bar, for the heart of the contraction dyssynchrony of the cardiac wall motion, the color coding being based on the equipment.

Concretely, the color display unit 21c sets a color bar CB for all the change curves including the respective control points $C_1$ and $C_2$, as shown in FIG. 6 by way of example. The color bar CB is in a color scheme which changes, for example, from green to red with the lapse of time by way of example. The color scheme of the color bar CB is not restricted to the change from green to red, but other colors may well be employed. The color bar CB is set at a length which includes the peak positions $P_1$ and $P_2$ of all the change curves including the respective control points $C_1$ and $C_2$. That is, the color bar CB is set in order to itemize the different peak positions $P_1$ and $P_2$ which are ascribable to the different timings of the tissue motions based on the systolic motion of the heart.

The color display unit 21c obtains the colors corresponding to the respective peak positions $P_1$ and $P_2$, from the color bar CB, and it codes these colors as the colors of the respective control points $C_1$ and $C_2$. By way of example, the peak position $P_1$ of the change curve of the control point $C_1$ is coded green. The peak position $P_2$ of the change curve of the control point $C_2$ is coded red. In this way, the colors of the peak positions of the change curves of the respective control points as have been obtained at all the pixels of the image data are coded.

Subsequently, at a step #8, the control unit 21 sends the image data of the movements of the respective control points $C_1$ and $C_2$ and the image data of the color coding to the video interface unit 19. The video interface unit 19 receives the image data for the B/M as are outputted from the first scan converter 17, or the image data for the CFM as are outputted from the second scan converter 18, and it combines the image data with the image data of the movements of the respective control points $C_1$ and $C_2$, the image data of the color coding, and various information items on an image, so as to display the laid-out ultrasonic image of the interior of the sample S on the monitor 20.

Figure 7:
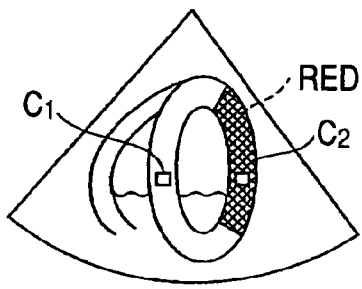
FIG. 7 is a diagram showing an example of the color-coded ultrasonic image of the heart of the contraction dyssynchrony as is displayed on the monitor of the equipment.

FIG. 7 shows an example of the ultrasonic image displayed on the monitor 20. The ultrasonic image displays the systolic motion of the heart as a dynamic image. This ultrasonic image indicates the image of the endosystole of the heart. The peak position $P_1$ of the change curve of, for example, the control point $C_1$ among all the control points is coded and displayed green. The peak position $P_2$ of the change curve of the control point $C_2$ is coded and displayed red. Accordingly, the colors of green and red are coded and displayed in the ultrasonic image of the heart. The difference of the coded colors of green and red indicates that the timings of the tissue motions based on the systolic motion of the heart are different. As a result, the contraction dyssynchrony of the cardiac wall motion can be diagnosed from the coded colors of the ultrasonic image displayed on the monitor 20.

Figure 8:
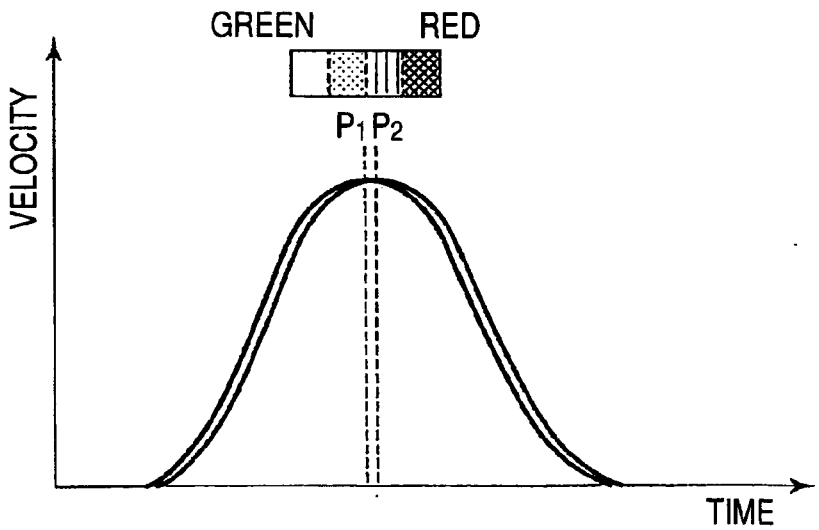
FIG. 8 is a diagram showing color coding which employs a color bar, for the normal heart, the color coding being based on the equipment.
Figure 9:
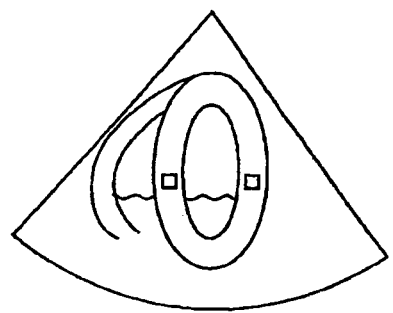
FIG. 9 is a diagram showing an example of the color-coded ultrasonic image of the normal heart as is displayed on the monitor of the equipment.

On the other hand, FIG. 8 shows a color bar CB which is set for the change curves of the respective control points $C_1$ and $C_2$ in the normal heart. The peak positions $P_1$ and $P_2$ lie at substantially the same positions. Thus, the peak position $P_1$ of the change curve of, for example, the control point $C_1$ among all the control points is coded and displayed green. Also the peak position $P_2$ of the change curve of the control point $C_2$ is coded and displayed green. Accordingly, the ultrasonic image displayed on the monitor 20 is coded and displayed in the single color of green as shown in FIG. 9 by way of example. As a result, the normal heart can be diagnosed from the coded color of the ultrasonic image displayed on the monitor 20.

By the way, in the above processing, the velocity images obtained by the tissue Doppler method may well be directly used, but a precise result is obtained in such a way that angular corrections are first made, and that velocity images subjected to the angular corrections are used.

In this manner, according to the first embodiment, control points $C_1$ and $C_2$, for example, are set on image data, the respective control points $C_1$ and $C_2$ between the image data of all frames $F_1$-$F_n$ are tracked, the velocity values of these control points $C_1$ and $C_2$ are evaluated, and the change curves of the respective control points $C_1$ and $C_2$ are obtained. In addition, colors which correspond to the peak positions $P_1$ and $P_2$ versus the lapse of time, in the change curves of these control points $C_1$ and $C_2$ are coded. Thus, the differences of the timings of tissue motions based on, for example, the systolic motion of the heart are displayed in terms of the differences of the colors.

As a result, when the heart is normal, the whole heart moves at substantially the same timing, and hence, an ultrasonic image is coded and displayed in the single color of, for example, green. In contrast, when the heart suffers from the contraction dyssynchrony of a cardiac wall motion, differences arise in the timings of the tissue motion based on the systolic motion of the heart. Thus, an ultrasonic image is coded and displayed, for example, green and red. Accordingly, the differences of the timings of the tissue motion based on the systolic motion of the heart can be visually recognized. The contraction dyssynchrony, for example, can be diagnosed.

Incidentally, although the first process unit 21a has evaluated the peak positions $P_1$ and $P_2$ in the change curves of, for example, the two control points $C_1$ and $C_2$ as shown in FIG. 4, this is not restrictive, but the positions of the centroids of the change curves or the positions of the standard deviations thereof may well be evaluated.

Next, the second embodiment of the invention will be described with reference to the drawings. Incidentally, the same parts as in the first embodiment shall be omitted from description, and only differences will be described.

The control unit 21 sets as control points, all pixels on image data which are sequentially created by the first scan converter 17 and the second scan converter 18. The control unit 21 detects the velocities of the motions of the sample S from the respective control points on the image data of individual frames created in succession.

The control unit 21 evaluates at least one sort of strain values, velocity gradient values and displacement values on the basis of the velocities of the motions of the sample S. The control unit 21 color-displays the differences of the timings of the motions in the sample S, on the monitor 20 on the basis of the temporal changes of at least one sort of the strain values, the velocity gradient values and the displacement values.

Figure 10:
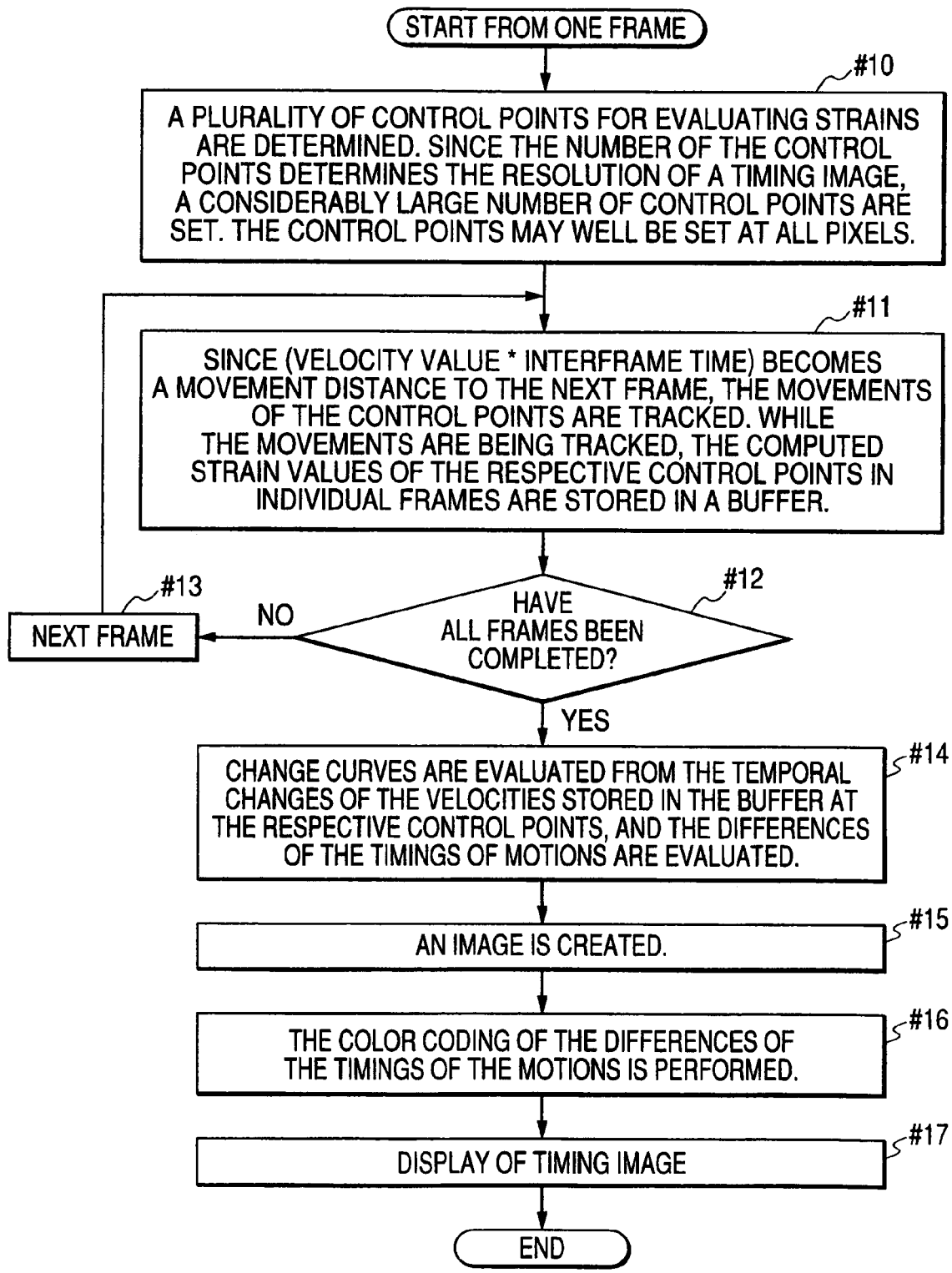
FIG. 10 is a control-process flow chart in the second embodiment of the ultrasonic diagnostic equipment according to the invention.

Next, the operation of the equipment configured as stated above will be described in conjunction with a control-process flow chart shown in FIG. 10.

The control unit 21 accepts the image data of individual frames created by the first and second scan converters 17 and 18, and it temporarily stores them in, for example, the storage unit 22. At a step #10, the control unit 21 sets control points at all the pixels of the image data of one frame accepted from each of the first and second scan converters 17 and 18. Control points may well be set at pixels which constitute at least some of the image data of one frame. Also here, however, only two of the control points shall be referred to for the sake of convenience.

At a step #11, the control unit 21 tracks the movements of the two control points $C_1$ and $C_2$ on the image data of a frame $F_2$ which is created later than the frame $F_1$. While tracking the respective control points $C_1$ and $C_2$ on the image data of the frames $F_1$ and $F_2$, the control unit 21 detects the movement velocities of the respective control points $C_1$ and $C_2$. The control unit 21 evaluates the individual strain values from the movement velocities of the respective control points $C_1$ and $C_2$. The strain values indicate how much the distances between the respective control points $C_1$ and $C_2$ have changed between, for example, the frames $F_1$ and $F_2$.

Accordingly, the strain value between the control point $C_1$ on the image data of the frame $F_1$ and the control point $C_1$ on the image data of the frame $F_2$ is evaluated. Simultaneously therewith, the strain value between the control point $C_2$ on the image data of the frame $F_1$ and the control point $C_2$ on the image data of the frame $F_2$ is evaluated. The control unit 21 stores the strain values of the respective control points $C_1$ and $C_2$ in, for example, the storage unit 22.

Subsequently, at a step #12, the control unit 21 judges whether or not the evaluations of the strain values of the respective control points $C_1$ and $C_2$ on the image data of all frames $F_1$-$F_n$ have been completed. If, as the result of the judgment, the evaluations have not been completed, the control unit 21 returns from a step #13 to the step #11, and it tracks the respective control points $C_1$ and $C_2$ on the image data of the frame $F_2$ and the next frame $F_3$. Thus, the control unit 21 evaluates the strain values of the respective control points $C_1$ and $C_2$ on the image data of the frames $F_2$ and $F_3$.

Thenceforth, the control unit 21 similarly iterates the steps #11 through #13, and it tracks the respective control points $C_1$ and $C_2$ between the image data of all the frames $F_1$-$F_n$, so as to evaluate the strain values between these control points $C_1$ and $C_2$.

When the strain values between the respective control points $C_1$ and $C_2$ between the image data of all the frames $F_1$-$F_n$ have been evaluated, the control unit 21 operates at a step #14 to read out the strain values between the respective control points $C_1$ and $C_2$ between the image data of all the frames $F_1$-$F_n$ as have been stored in the storage unit 22, and to evaluate individual change curves which indicate the temporal changes of the strain values at the respective control points $C_1$ and $C_2$. Since the change curves of the control points are evaluated at all the pixels in the image data of all the frames $F_1$-$F_n$, the change curves of the control points in the whole heart are evaluated.

Subsequently, at a step #15, the control unit 21 creates the image data of the movements of, for example, the respective control points $C_1$ and $C_2$, on the basis of all the change curves including the respective control points $C_1$ and $C_2$ as have been evaluated at all the pixels of the image data.

Subsequently, the first process unit 21a evaluates peak positions in the individual change curves of all the control points including the respective control points $C_1$ and $C_2$.

Subsequently, at a step #16, the second process unit 21b displays the differences of the timings of the tissue motions based on the systolic motion of the heart or the like sample S, on the monitor 20 on the basis of all the change curves including the respective control points $C_1$ and $C_2$ as have been evaluated at all the pixels of the image data.

Concretely, the color display unit 21c sets a color bar CB for all the change curves including the respective control points $C_1$ and $C_2$, similar to the one shown in FIG. 6 by way of example.

The color display unit 21c obtains the colors corresponding to the respective peak positions $P_1$ and $P_2$, from the color bar CB, and it codes these colors as the colors of the respective control points $C_1$ and $C_2$. By way of example, the peak position $P_1$ of the change curve of the control point $C_1$ is coded green. The peak position $P_2$ of the change curve of the control point $C_2$ is coded red. In this way, the colors of the peak positions of the change curves of the respective control points as have been obtained at all the pixels of the image data are coded.

Subsequently, at a step #17, the control unit 21 sends the image data of the movements of the respective control points $C_1$ and $C_2$ and the image data of the color coding to the video interface unit 19. The video interface unit 19 receives the image data for the B/M as are outputted from the first scan converter 17, or the image data for the CFM as are outputted from the second scan converter 18, and it combines the image data with the image data of the movements of the respective control points $C_1$ and $C_2$, the image data of the color coding, and various information items on an image, so as to display the laid-out ultrasonic image of the interior of the sample S on the monitor 20.

As a result, if the sample S suffers from the contraction dyssynchrony of a cardiac wall motion, the ultrasonic image which is displayed on the monitor 20 are coded green and red, similarly to the ultrasonic image shown in FIG. 7. Accordingly, the contraction dyssynchrony of the cardiac wall motion can be recognized from the fact that the coded colors are the different ones of green and red.

In contrast, if the sample S is the normal heart, the ultrasonic image which is displayed on the monitor 20 is coded and displayed in the single color of green as shown in FIG. 9 by way of example. Thus, the normal heart can be recognized.

In this manner, according to the second embodiment, control points $C_1$ and $C_2$, for example, are set on image data, the respective control points $C_1$ and $C_2$ between the image data of all frames $F_1$-$F_n$ are tracked, the strain values at the respective control points $C_1$ and $C_2$ in the individual frames are evaluated, and the change curves of the strain values at the respective control points $C_1$ and $C_2$ are obtained. Thus, the same advantage as in the first embodiment can be achieved.

The invention is not restricted to the foregoing embodiments, but it may well be modified as stated below.

By way of example, the personal computer 23 may well accept respective image data which are outputted from the first and second scan converters 17 and 18. The personal computer 23 may well process the image data and analyze, for example, the motion of the tissue of the sample S.

The control unit 21 need not always evaluate the velocity values or strain values of two control points $C_1$ and $C_2$, but it may well evaluate at least one sort of velocity gradient values and displacement values. The velocity gradient value is acquired in such a way that the velocity difference of two points spaced a fixed distance in a movement velocity distribution obtained by the tissue Doppler method is divided by the distance between the two points. The acquisitions of such velocity gradient values are performed at all the pixels of the respective image data. The displacement value is evaluated as the quantity of the movements of the tissue by integrating values obtained in such a way that the velocity values of individual frames which are included in a fixed time period in the movement velocity distribution obtained by the tissue Doppler method are multiplied by an interframe time difference. The displacement value indicates how much the tissue within the sample S has moved within any desired time period. The control unit 21 evaluates change curves which indicate the temporal changes of the respective velocity gradient values or the respective displacement values at all control points.

In each of the foregoing embodiments, the velocity values, strain values, velocity gradient values or displacement values of the control points are evaluated and are stored in the storage unit 22, whereupon the change curves of the velocity values, strain values, velocity gradient values or displacement values are automatically evaluated. This is not restrictive, but the control unit 21 may well once store the velocity values, strain values, velocity gradient values or displacement values of the control points in the storage unit 22. Thereafter, the control unit 21 may well wait for the input of, for example, a user's instruction. When the user's instruction is inputted to the control unit 21, this control unit 21 may well evaluate the change curves of the velocity values, strain values, velocity gradient values or displacement values.

Otherwise, the configuration of the ultrasonic diagnostic equipment, the function of the control unit, the timing image generation procedure and the contents thereof, the sorts of the change quantities of the control points, and so forth, can be variously modified and performed within a scope not departing from the purport of the invention.

What is claimed is:

1. An ultrasonic diagnostic equipment, comprising:
   an ultrasonic probe configured to transmit ultrasonic waves into a heart, receive reflected waves from the heart, and output reception signals;
   image data creation circuitry configured to create a plurality of images of the heart based on the reception signals from the ultrasonic probe;
   processing circuitry configured to set a plurality of control points at different positions on at least one of the plurality of images created by the image data creation circuitry, track the respective control points on remaining images of the plurality of images, obtain a plurality of change curves that indicate temporal changes of measured physical quantities of a plurality of positions of the heart based on the temporal change of positions of the tracked respective control points, determine a peak time for each of the plurality of change curves and generate an image that graphically indicates differences between the peak times respectively of the plurality of local positions; and
   a color display configured to display the change curves and a color bar that has a length longer than a distance between the peak times in the displayed changed curves, wherein the color bar indicates different colors along a time direction of the change curves.

2. The ultrasonic diagnostic equipment as defined in claim 1, wherein the processing circuitry is configured to set pixels in the image data as the control points.

3. The ultrasonic diagnostic equipment as defined in claim 1, wherein the processing circuitry is configured to set the control points at all pixels in the image data or some of the pixels.

4. The ultrasonic diagnostic equipment as defined in claim 1, wherein:
   the heart contains a tissue; and
   processing circuitry is further configured to
     evaluate the peak times of the change curves of the motions of the tissue of the heart; and evaluate the differences of the motions of the tissue based on the evaluated peak times, and to display the differences of the motions of the tissue.

5. The ultrasonic diagnostic equipment as defined in claim 4, wherein the color display displays the differences of the motions of the tissue of the heart using plural colors, wherein each respective peak time is converted into a color to be displayed at the respective control point.

6. The ultrasonic diagnostic equipment as defined in claim 5, wherein:
the heart performs a contraction motion; and
the color display is further configured to display the differences of the motions of the tissue at individual parts of the heart based on the contraction motion of the heart using plural colors.

7. The ultrasonic diagnostic equipment as defined in claim 4, wherein the processing circuitry is further configured to evaluate centroids or standard deviations of the temporal changes of the velocities of the motions of the tissue of the heart.

8. The ultrasonic diagnostic equipment as defined in claim 5,
wherein the color display is further configured to display an ultrasonic image based on the image data sequentially created by the image data creation circuitry, and present the color display of the differences of the motions of the tissue in superposition on the ultrasonic image.

9. A control method for an ultrasonic diagnostic equipment, comprising:
transmitting ultrasonic waves from an ultrasonic probe into a heart;
receiving reflected waves from the heart;
outputting reception signals;
creating a plurality of images of the heart based on the reception signals;
setting a plurality of control points at different positions on at least one of the plurality of images;
tracking the respective control points on remaining images of the plurality of images;
obtaining a plurality of change curves that indicate temporal changes of measured physical quantities of a plurality of local positions of the heart based on the temporal change of positions of the tracked respective control points;
determining a peak time for each of the plurality of change curves; generating an image that graphically indicates differences between the peak times respectively of the plurality of local positions; and
displaying the change curves and a color bar that has a length longer than a distance between the peak times in the displayed changed curves, wherein the color bar indicates different colors along a time direction of the change curves.

* * * * *